United States Patent [19]

Hoffman, Jr. et al.

[11] 3,986,828

[45] Oct. 19, 1976

[54] POLYMER FABRIC COMPACTING PROCESS

[75] Inventors: Harmon L. Hoffman, Jr., Wyckoff; Jacob Tolsma, North Haledon, both of N.J.

[73] Assignee: Meadox Medicals, Inc., Oakland, N.J.

[22] Filed: Mar. 5, 1974

[21] Appl. No.: 448,447

[52] U.S. Cl. .............................. 8/115.5; 8/149.1; 8/149.2
[51] Int. Cl.² ........................................ D06B 13/00
[58] Field of Search ............... 8/115.5, 149.2, 149.1

[56] References Cited
UNITED STATES PATENTS 3,485,574  12/1969  Miller et al. ..................... 8/115.5

*Primary Examiner*—Stephen J. Lechert, Jr.
*Attorney, Agent, or Firm*—Blum, Moscovitz, Friedman & Kaplan

[57] ABSTRACT

Polyester fabric which may be in the form of a warp-knitted lock-stitched or tricot-stitched tubular construction is compacted by treatment with $NO_2$ either in the gaseous phase or in solution. The product, after neutralization, washing and crimping is suitable for vascular prostheses. In one form, the compacted product is crimped and bifurcated. Shrinkage in both the longitudinal and transverse directions is at least 30%. The porosity of the fabric is reduced by the compacting treatment.

37 Claims, 11 Drawing Figures

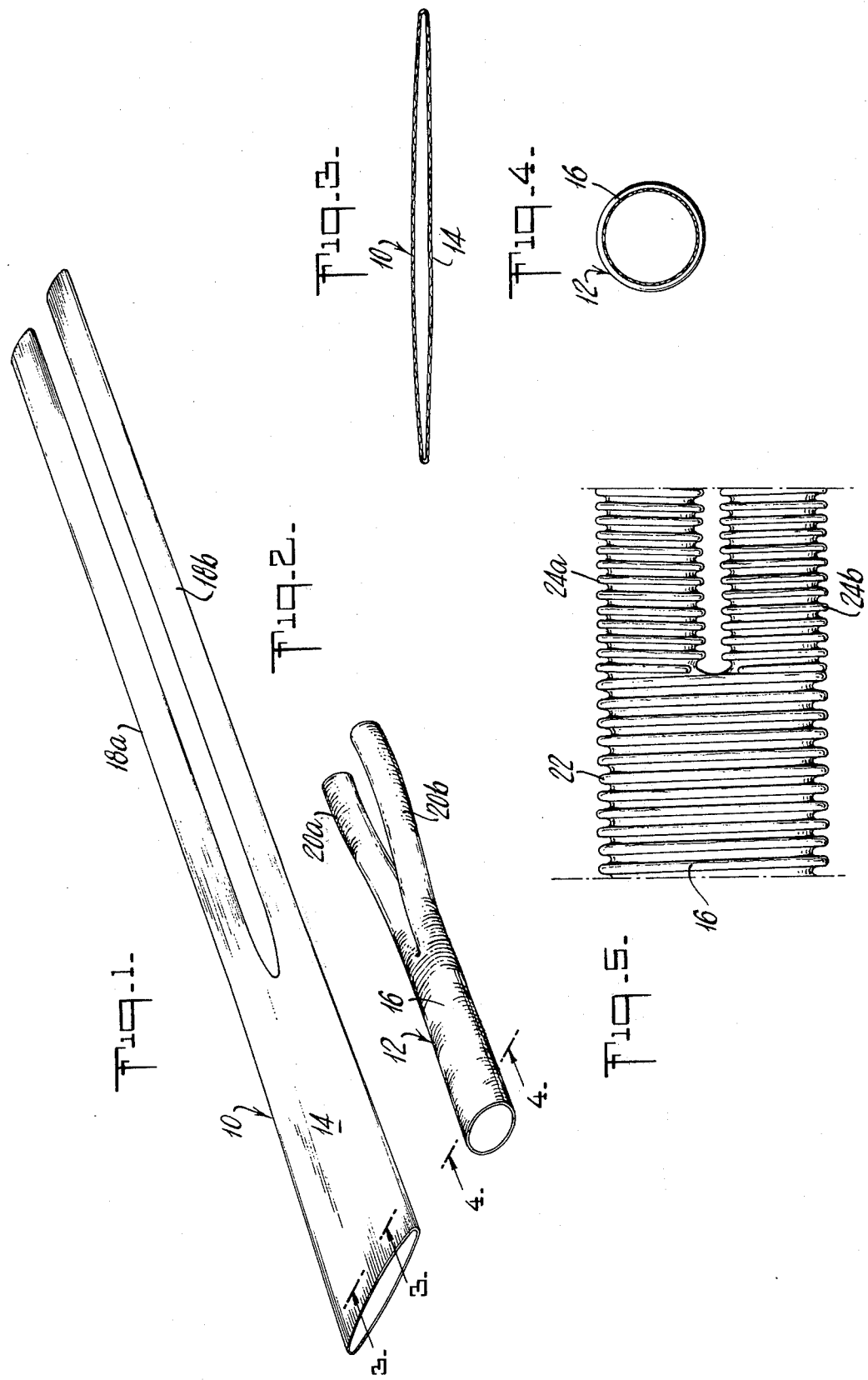

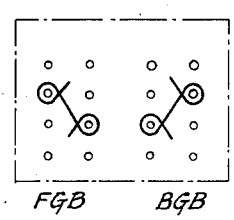
Fig.6a.
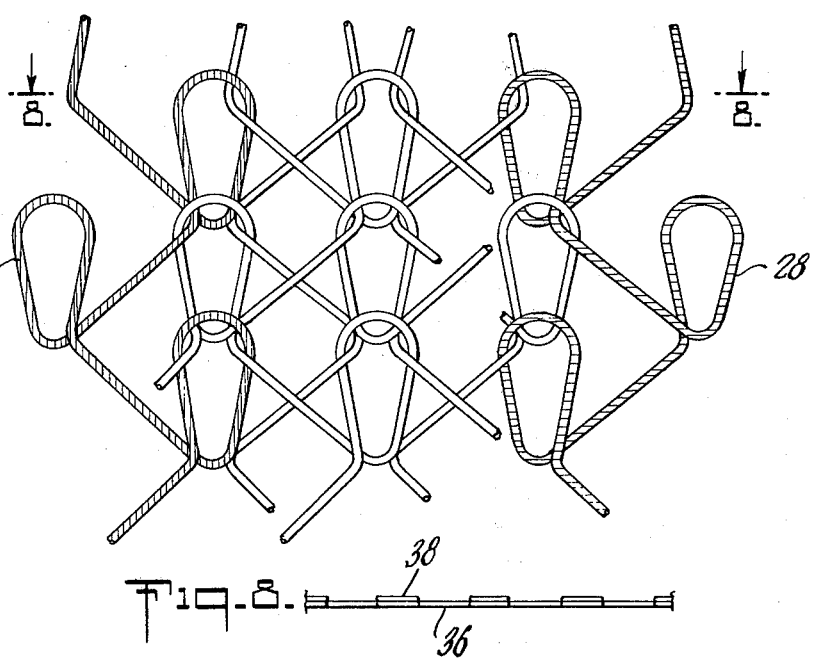
Fig.6.
Fig.8.
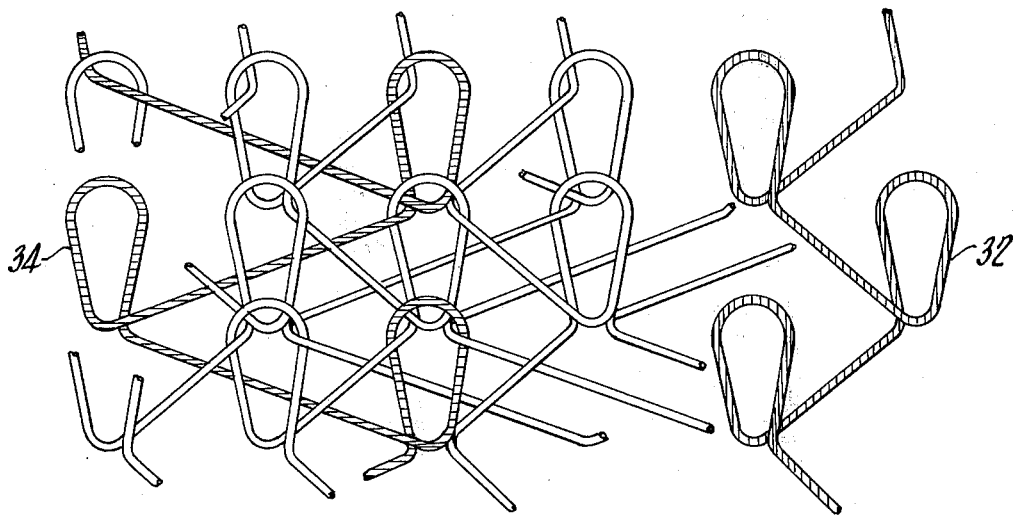
Fig.7.
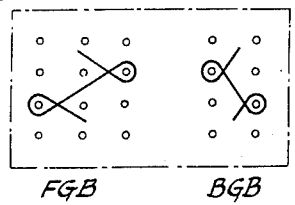
Fig.7a.

POLYMER FABRIC COMPACTING PROCESS

BACKGROUND OF THE INVENTION

Knitted, braided, non-woven and woven textile materials, whether of natural of of synthetic fibrous material are usually porous. Over the past few years it has been found that a number of textiles of synthetic fibers are compatible with the human body, so that such textiles either as flat fabrics or in tubular form are suitable for use as patches or as replacements for portions of arteries or veins. Vascular prostheses constitute a particularly important use for such materials in that they can be used for repair and replacement of vessels in both humans and animals. Among the most important of such applications, are those in which the structure must be bifurcated.

For incorporation of such material into the human body or into an animal, the material structure must have certain physical characteristics as well as chemical characteristics. The chemical characteristics, of course, are those which influence rejection by the individual, whether human or animal, into which the structure is placed. Teflon has frequently been used. However, polyesters, and in particular the condensate of terephthalic acid with polyethylene glycol, have been found to be most satisfactory so far as chemical characteristics are concerned.

With respect to physical characteristics, the fabric must have a porosity great enough so that there can be ingrowth of fibrous tissue, a process which is termed fibrosis, so that the fabric can be completely covered with fibrous tissue characteristic of the healing process. In addition, the porosity must not be so great that excessive blood transfer or hemorrhaging therethrough will result in a hematoma or or collection or pooling of blood adjacent to the vessel.

As a step in preparing the fabric for implantation preclotting of blood on the fabric prior to implantation is generally carried out. Finally, tests have shown that the thickness of the fabric should be about 0.1 mm to 1.0 mm, approximately the thickness of that portion of the circulatory system to be repaired or replaced. Further characteristics which must be considered are flexibility, extensibility, strength and resilience sufficient to withstand blood pressure. Also, the construction of the fabric is preferably such that ravelling does not occur. This is most important when the graft is implanted into a vein or artery. Also, it is necessary that the fabric be capable of withstanding the conditions involved in sterilizing same.

As aforenoted, the porosity of the fabric is critical due to the fact that the body heals by fibrosis. Moreover, in considering the porosity of a fabric it is necessary that the uniformity of the porosity over the complete area of the structure be taken into account. As is evident, where the porosity varies very widely, then hemorrhaging could take place in one section of the structure although the average porosity of same would appear to be appropriate for implantation. So far as the usual woven or knitted fabric is concerned, where multi-filament thread is used, the flow through the fabric is a function of the spacing of the filaments which may or may not be crimped. As is evident, the degree of control achievable in the spacing between the filaments comprising a single strand of yarn is not great. Consequently, it is difficult to control the uniformity of porosity of a fabric which is woven or which is knitted by the usual techniques. In contrast, fabrics having a warp-knitted, lock-stitched or tricot-stitched construction can be made so that they present interstices which are polygons, usually three-sided, of relatively uniform size. Under such circumstances, the porosity of a fabric can be well controlled. However, even when knitted on Raschel machines using the finest needles and filament threads, i.e., yarns, the porosity of the resultant fabric prior to compaction is excessive so far as implantation is concerned.

The porosity of knitted material conventionally is presented as a measurement of the Wesolowski scale. To carry out the Wesolowski test, a piece of a test fabric is clamped against a flat surface having an orifice therein. Water is forced against the opposite side of the fabric at a constant pressure of 120 mm of mercury. The rate at which water passes through the fabric is expressed in $ml/minute/cm^2$ of fabric. The value of 24,000 on the Wesolowski scale corresponds to free flow. For a vascular graft, the porosity of the fabric should be from about 30 to about 5,500, and preferably should lie between 1,200 and 4,000. Knitted fabric, whether of tubing or flat stock, even when knitted on the finest gauge double-needle bar Raschel machine available and with filament yarns, usually gives a reading in excess of 7,500 and may exceed 8,500 on the Wesolowski scale. Consequently, to reduce the porosity of the material, the fabric must be uniformly shrunk. The shrinkage in the wale direction of the fabric should be at least 30% and preferably should be at least about 40%.

In view of the increasing use of implanted fabric, particularly for vascular grafts, there is need for a process by which such compaction can be reliably carried out at relatively low cost. Furthermore, there is need for fabric having the properties described above.

SUMMARY OF THE INVENTION

The compound $NO_2$ has been found to shrink, i.e., compact, at least partly oriented polyester fabrics linearly by as much as 30%, and by intensive treatment in excess of 40%. The compound has been found to be particularly effective in compacting the high molecular weight condensate of terephthalic acid and ethylene glycol.

The compound can be used in the gaseous phase or in solution. A preferred solvent is methylene chloride where the $NO_2$ constitutes from 5% to 18% by weight of the solution. The shrinkage is increased when the solution is moist.

After treatment of fabric with a compacting agent in accordance with the present invention, the fabric must be washed with a neutralizing agent such as dilute sodium carbonate and with a detergent, after which it is washed with tap water or distilled water. The neutralization step and washing with detergent may be combined by using a dilute solution of alkali including a suitable detergent.

There is no restriction on the type of fabric with respect to construction on which the compacting method may be used. It is satisfactory for use on flat, woven and knit fabrics, as well as circular knit and the wide range of warp-knit tubular fabrics which are resistant to ravelling. The shrinkage resulting from the process of the present invention is essentially equal in both directions whether wale and course or warp and weft. It is particularly suitable for use on fabrics made of multi-filament thread because of the large exposed surface area.

Tubular, crimped, polyester grafts which are warp-knitted and either lock-stitched or tricot-stitched and which have been compacted by the above process provided particularly good control of porosity between the limits suitable for ingrowth of tissue by fibrosis and for avoiding hemorrhaging.

Accordingly, an object of the present invention is a method of compacting polyester fabrics uniformly.

Another object of the present invention is a method of compacting polyester fabrics rapidly and at low cost.

A further object of the present invention is a method of compacting polyester fabrics which gives close control of the porosity.

An important object of the present invention is a warp-knitted fabric, either lock-stitched or tricot-stitched, which is tubular and crimped and which has been compacted by the process of the present invention.

Still another object of the present invention is a process of compacting fabrics constructed of multi-filament yarn, either texturized or untexturized where the yarn is a polymeric condensate of terephthalic acid and ethylene glycol.

Yet another object of the present invention is a method of compacting fabric of multi-filament yarn, texturized or untexturized, where the hand is excellent as a result of lack of adhesion between the filaments.

Still other objects and advantages of the invention will in part be obvious and will in part be apparent from the specification.

The invention accordingly comprises the several steps and the relation of one or more of such steps with respect to each of the others, and the article possessing the features, properties, and the relation of elements, wich are exemplified in the following detailed disclosure, and the scope of the invention will be indicated in the claims.

BRIEF DESCRIPTION OF THE DRAWING

For a fuller understanding of the invention, reference is had to the following description taken in connection with the accompanying drawings, in which:

FIG. 1 is a perspective illustration of a knitted tube compacted in accordance with the present invention, prior to crimping;

FIG. 2 is a perspective illustration of the knitted tube of FIG. 1 subsequent to crimping;

FIG. 3 is a transverse section of the structure of FIG. 1 taken along line 3—3 of FIG. 1;

FIG. 4 is a transverse section of the structure of FIG. 2 taken along the line 4—4 of FIG. 2;

FIG. 5 is an illustration of a portion of the crimped structure of FIG. 2 in enlarged scale relative to FIG. 2, showing the crotch of said structure;

FIG. 6 is a diagrammatic representation of a portion of a knitted wall having tricot-stitches;

FIG. 6a is a fragmentary point paper diagram of the knitted structure of FIG. 6;

FIG. 7 is a diagrammatic illustration of a lock-knit structure;

FIG. 7a is a fragmentary point paper diagram of the lock-knit structure of FIG. 7;

FIG. 8 is a transverse schematic fragmentary section taken along 8—8 of FIG. 6, showing the knitted formations which result from the knitted structure of FIG. 6.

DESCRIPTION OF THE PREFERRED EMBODIMENTS

Figure 9:
FIG. 9 is a representation in greatly enlarged scale of a fragment of a warp-knitted lock-stitched structure showing the formation of an interstice by multi-filament threads.

Fabrics of polyesters, and, in particular constructions of at least partly oriented fibers of polymeric condensate of terephthalic acid and polyethylene glycol are readily compacted by $NO_2$. For carrying out the compacting process, the fabric can be exposed either to the gas or to nitrogen dioxide in solution. A suitable solvent is methylene chloride, $CH_2Cl_2$. A suitable concentration range for the nitrogen dioxide in the solvent, preferably methylene chloride is from 5 to 18%. A preferred range is from 8 to 12%.

In general, the reaction of the fabric with $NO_2$ in gaseous form is relatively slow, periods of about two hours being required to obtain adequate shrinkage. In the case of a warp-knitted fabric of 40 denier thread, tubing samples shrank 33% in width and 40% in length. A piece of tubing having a count of 38 wales by 59 courses shrank to 64 wales by 94 courses. A similar result was obtained with a polyester fabric of 70 denier thread. In each case, the thread consisted of a large number of filaments, the number of filaments per thread normally being in the range of about 34 to 50. It will be noted that the shrinkages in width and in length do not differ greatly.

Compacting of polyesters, and, in particular, the high molecular condensate of terephthalic acid and polyethylene glycol, proceeds much more rapidly when the $NO_2$ is dissolved in methylene chloride and the shrinkage is greater when the solution is moist (0.08% to 0.3% water). Uncompacted swatches of 40 denier and 70 denier Dacron (the high molecular weight condensate of terephthalic acid and polyethylene glycol made by Dupont) when immersed for two minutes in a 5% solution of $NO_2$ in methylene chloride went from counts of 33 × 59 and 36 × 54 respectively to 55 × 87 and 48 × 74. When uncompacted swatches of 40 and 70 denier Dacron were immersed for one minute in an 8% solution of $NO_2$ in methylene chloride the counts of the treated tubes became, respectively, 60 × 90 and 48 × 76. The Wesolowski porosities of swatches measured at 120 mm pressure were 5,110 ml/min/cm$^2$ and 2,930 ml/min/cm$^2$, respectively. In general, compacted 40 denier fabric has counts of 55 – 65 wales × 85 – 95 courses. For 70 denier compacted fabric the counts are 45–55 wales × 74–84 courses.

A series of tests showed that effective compaction could be obtained where the $NO_2$ dissolved in moist methylene chloride constituted from 5 to 18% by weight. However, compaction to the desired extent took place more rapidly when the range of $NO_2$ in the moist solvent was from 8 to 12% by weight. Moreover, a compaction of at least 30% in both directions can be obtained in as little as 30 seconds when the percentage of $NO_2$ is in the range of 8 to 12%.

In general, fabrics before compacting have counts of about 33 × 59 for fabric of 40 denier yarn and 36 × 54 for 70 denier yarn. When treated with a solution of $NO_2$ in dry methylene chloride the count for 40 denier goes to 55 – 62 × 84 – 90 and for 70 denier yarn goes to 45 – 50 × 74 – 80. The shrinkage depends on the treatment time, the $NO_2$ concentration and the degree of orientation of the yarn. In the presence of 0.2% of water, the count goes to 55 – 65 × 85 – 95 for 40 denier yarn and 45 – 55 × 74 – 84 for 70 denier yarn. It should be noted that the water is in solution and is not a separate phase. Prior to compaction, the Wesolowski value of the fabric is preferably above 20,000.

If the compacted fabric is removed from the solution and allowed to dry, the filaments and the threads tend to stick to each other. Consequently, a washing procedure must be followed. As the first step, the compacted fabric is immersed in a dilute alkaline solution, where the alkalinity and volume of the solution are such that after washing the fabric the solution has a pH of at least 7.0. A suitable solution can be prepared by dissolving from 0.5 to 4.0 of $Na_2CO_3$/liter of water, where the water may be either tap water or distilled water. Also, it is necessary to wash the fabric with the detergent solution. This can be carried out as a separate step, or the detergent can be combined with the dilute alkaline solution. Suitable detergents are octyl phenoxy polyethoxy ethanol, polyoxyethylene ether alcohol, and the condensate of ethylene oxide with hydrophobic bases formed by condensing propylene oxide with propylene glycol. Finally, the fabric is washed with water which may be either tap water or distilled water. The treatment results in a fabric with an excellent hand.

A number of warp-knitted tricot, bifurcated tubes of 40 denier and 70 denier threads were treated with moist reagent. The counts of the treated tubes were 60 × 86 and 50 × 76 for the 40 denier and 70 denier fabrics, respectively. The porosities of the treated tubes were 5,310 ml/min/cm$^2$ and 2,890 ml/min/cm$^2$, respectively. It should be noted that tubes in this state have virtually no rigidity and are essentially shapeless as well as non-extensible. However, after spiral crimping by conventional techniques, the tubes become flexible, extensible, relatively rigid, and, consistent with their construction, nonravelling. After crimping, the porosities of the treated tubes are found to be substantially smaller. For the 40 denier fabric, the porosity on the Wesolowski scale is 1,670 ml/min/cm$^2$ and for the 70 denier fabric is 1,270 ml/min/cm$^2$.

A suitable porosity range for a compacted fabric prior to crimping is 30 – 5,500; a preferred range is 1,200 – 4,000. Subsequent to crimping the preferred range is 800 – 2,500.

A wide variety of types of knit can be prepared by the warp-knitting process. For use in vascular prostheses, warpknitted, lock-stitched tricot fabrics are preferred. All types of warp-knitted fabrics are compacted readily by the treatment described. A major advantage shown by the warp-knitted tricot fabric is that there are definite triangular openings or interstices through the fabric. (See FIG. 9). This type of knit makes it possible to form such interstices which are quite uniform in size. As a result, all portions of a patch or a graft have the same porosity so that tissue ingrowth and the rate of transfer of blood through the fabric are also uniform over the entire area of the structure. The fact that there are regular openings or interstices through the fabric makes it possible to control the porosity as measured on the Wesolowski scale quite closely. In contrast, circular knit fabrics have no regular interstices so that flow therethrough is primarily a matter of the haphazard spacing of the filaments in multi-filament thread. Consequently, the degree of control of porosity attainable with a warp-knit tricot or lock-stitched fabric is substantially greater than that obtainable with a circular knit fabric.

A major advantage of the use of multi-filament thread is that a large surface area is presented, the high speed of compaction resulting from treatment with $NO_2$ in solution being attributable to this factor.

It will thus be seen that the objects set forth above, among those made apparent from the preceding description, are efficiently attained, and, since certain changes may be made in carrying out the above method and in the article set forth without departing from the spirit and scope of the invention, it is intended that all matter contained in the above description and shown in the accompanying drawings shall be interpreted as illustrative and not in a limiting sence.

It is also to be understood that the following claims are intended to cover all of the generic and specific features of the invention herein described, and all statements of the scope of the invention which, as a matter of language, might be said to fall therebetween.

What is claimed is:

1. A method of preparing a synthetic vascular graft, comprising the step of treating a porous polyester fabric with a member of the group consisting of gaseous $NO_2$ and $NO_2$ in solution in $CH_2Cl_2$ under conditions such that said fabric is shrunk and the porosity thereof is reduced, thereby compacting said fabric.

2. The method as defined in claim 1 wherein said solution of $NO_2$ in $CH_2Cl_2$ contains 0.08 to 0.3% water.

3. The method as defined in claim 1 wherein the ratio of $NO_2$ to $CH_2Cl_2$ ranges from 5:95 to 18:82 by weight.

4. The method as defined in claim 1 wherein thee ratio of $NO_2$ to $CH_2Cl_2$ ranges from 8:92 to 10:90 by weight.

5. The method as defined in claim 1 wherein said polyester is a terephthalic acid ethylene glycol condensate.

6. The method as defined in claim 1 wherein the polyester of said fabric is in the form of a multi-filament thread.

7. The method as defined in claim 1, further comprising the steps of washing said treated fabric with a dilute alkaline solution in sufficient quantity so that the final pH of said solution subsequent to washing the fabric therein is at least 7.0, washing said fabric with a detergent solution, and washing said fabric with water.

8. The method as defined in claim 7 wherein said steps of washing with dilute alkaline solution and with detergent solution are carried out simultaneously by utilizing a dilute alkaline solution containing detergent.

9. The method as defined in claim 7 wherein said dilute alkaline solution consists of about 0.5 to 4.0 g of $Na_2CO_3$/liter of water.

10. The method as defined in claim 7 wherein said detergent solution contains at least one member of the group consisting of octyl phenoxy polyethoxy ethanol, polyoxyethylene ether alcohol, and condensate of ethylene oxide with hydrophobic bases formed by condensing propylene oxide with propylene glycol.

11. The method as defined in claim 1 wherein the time of treatment of said fabric with said member of said group is sufficient to shrink the fabric by at least 30% in the wale direction.

12. The method defined in claim 1 wherein the time of treatment is sufficient to shrink said fabric by at least 40% in the wale direction.

13. The method defined in claim 1 wherein said fabric is a warp-knitted tricot fabric.

14. The method as defined in claim 11 wherein said fabric is tubular in form.

15. The method as defined in claim 14 wherein said tubular fabric is bifurcated.

16. The method as defined in claim 1 wherein said knitted polyester fabric is treated with gaseous $NO_2$ for at least about two hours.

17. The method as defined in claim 1 wherein said fabric is treated with said solution of $NO_2$ in $CH_2Cl_2$ for at least about 30 seconds.

18. The method as defined in claim 1 wherein said fabric is knitted of a yarn between 40 and 70 denier.

19. The method as defined in claim 18 wherein said 40 denier fabric after compaction has about 55 – 62 wales × 84 – 90 courses and said 70 denier fabric after compaction has about 45 – 50 wales × 74 – 80 courses.

20. The method as defined in claim 2 wherein said fabric is knitted of a yarn between 40 and 70 denier.

21. The method as defined in claim 20 wherein said 40 denier fabric after compaction has about 55 – 65 wales × 85 – 95 courses and said 70 denier fabric after compaction has about 45 – 55 wales × 74 – 84 courses.

22. The method as defined in claim 1 wherein said polyester fabric prior to treatment has a porosity on the Wesolowski scale above about 20,000.

23. The method of claim 1 wherein said polyester fabric prior to said treatment has a porosity on the Wesolowski scale above about 20,000 and the time of treatment is such as to reduce the porosity of a compacted fabric to between about 30 and about 5,500.

24. The method as defined in claim 23, wherein the time of treatment is such as to reduce the porosity on the Wesolowski scale to between about 1,200 and 4,000.

25. The method as defined in claim 7 wherein said method further comprises the steps of preparing said fabric in the form of a warp-knitted tricot tube prior to compacting said fabric and drying said compacted tube and crimping same into a spiral, thereby imparting relative rigidity to said tube and rendering said tube spring-like longitudinally.

26. The method as defined in claim 25 wherein the treatment is such that said crimped tube has a porosity on the Wesolowski scale between about 800 and 2,500.

27. The method as defined in claim 25 wherein said tube is bifurcated.

28. A polyester fabric compacted by a member of the group consisting of $NO_2$ and a solution of $NO_2$ in $CH_2Cl_2$.

29. The fabric as defined in claim 28 wherein said solution contains 0.08% – 0.3% of water.

30. The fabric as defined in claim 29 wherein said fabric is a knitted fabric and is knitted of a multi-filament thread having a denier between 40 and 70.

31. The compacted knitted fabric of claim 29 wherein said fabric has between 45 and 65 wales × 74 and 95 courses.

32. The compacted fabric as defined in claim 28, wherein said fabric is of warp-knitted tricot construction and is tubular in form.

33. The compacted knitted fabric as defined in claim 32 wherein said tubular fabric is spiral-crimped, thereby imparting rigidity to said construction and making same elastic longitudinally.

34. The compacted knitted fabric as defined in claim 33 wherein said tubular fabric is bifurcated.

35. The compacted knitted fabric as defined in claim 33 wherein the porosity of said material on the Wesolowski scale lies between about 30 to 5,500.

36. The compacted knitted fabric as defined in claim 33 wherein the porosity of said material on the Wesolowski scale lies between about 1,200 to 4,000.

37. A knitted fabric as defined in claim 28 wherein said polyester is of multi-filament, polymeric terephthalic acid ethylene glycol condensate having a denier of 40 – 70 and is in the form of crimped bifurcated tube.

\* \* \* \* \*